United States Patent [19]
Furui et al.

[11] Patent Number: 5,783,427
[45] Date of Patent: Jul. 21, 1998

[54] PROCESS FOR PREPARING D-AMINO ACIDS

[75] Inventors: Masakatsu Furui, Takatsuki; Eiji Takahashi, Osaka; Hiroyasu Seko, Nara-ken; Takeji Shibatani, Kobe, all of Japan

[73] Assignee: Tanabe Seiyaku Co., Ltd., Osaka, Japan

[21] Appl. No.: 621,970

[22] Filed: Mar. 26, 1996

[30] Foreign Application Priority Data

| Mar. 28, 1995 | [JP] | Japan | 7-068459 |
| Sep. 7, 1995 | [JP] | Japan | 7-229899 |
| Jan. 23, 1996 | [JP] | Japan | 8-009452 |

[51] Int. Cl.[6] ............. C12P 13/08; C12P 13/06; C12P 41/00
[52] U.S. Cl. ............. 435/115; 435/107; 435/113; 435/116; 435/252.1; 435/280; 435/873
[58] Field of Search ............. 435/113, 280, 435/107, 116, 115, 873, 252.1

[56] References Cited

U.S. PATENT DOCUMENTS

| 5,068,187 | 11/1991 | Takeichi et al. | 435/113 |
| 5,081,024 | 1/1992 | Kuwahara et al. | 435/110 |
| 5,219,731 | 6/1993 | Sih | 435/18 |
| 5,300,430 | 4/1994 | Shapiro et al. | 435/280 |
| 5,552,318 | 9/1996 | Houng et al. | 435/280 |

FOREIGN PATENT DOCUMENTS

| 0 181 675 | 5/1986 | European Pat. Off. |
| 0 542 222 | 5/1993 | European Pat. Off. |
| 92/10579 | 12/1991 | WIPO |

OTHER PUBLICATIONS

APS Abstract JP62–96454 May 2, 1987 Nohira et al.
APS Abstract J61–186355 Aug. 20, 1986 Miyazawa et al.
Derwent Abstract WPIL 88–088336/13 Agency Ind Sci Tech "D–amino acid prodn." J630039598 Feb. 1988.
Derwent Abstract Biotech 88–06093 Agency Ind Sci "Production amino acids" J63039598 (equiv above) Feb. 1988.
Derewent Abstract Biotech 90–02649 Mitsubishi Gas Chem "Preparation of a D–alpha amino acid" J01262798 Oct. 1989.
Derwent Abstract JAPIO Tagawa et al "Production of Optically Active D–amino Acid" J06022789 Feb. 1994.
Derwent Abstract 70–39911R/22 Banyu Seiyaku KK "Production of d–amino acid" J70015433 May 1970.
Derwent Abstract WPI 73–41405u/29 Kyowa Hakko Kogyo Co Ltd "Optical Resolution of amino acids" J73023915 Jul. 1973.
Applied and Environmental Microbiology, vol. 54, pp. 984–989 (1988), Francis et al., "Anaerobic Microbial Dissolution of Transition and Heavy Metal Oxides".
Journal of Fermentation Technology, vol. 56, No. 5, pp. 492–498 (1978), Satomi Takahashi et al, "Purification, Crystallization and Properties of Hydantoinase from *Pseudomonas striata*".
Agric. Biol. Chem., vol. 51, pp. 715–719 (1987), Kenzo Yokozeki et al., "Optimal Conditions for the Enzymatic Production of D–Amino Acids from the Corresponding 5–Substituted Hydantoins".
Journal of Biotechnology, vol. 8, pp. 243–248 (1988), Nobuyoshi Nakajima et al., "Enantioselective Synethesis of Various D–amino Acids by a Multi–Enzyme System".
Bulletin of the Institute for Chemical Research, Kyoto University., vol. 65, No. 3, No. 3, pp. 141–143 (1987), Nobuyoshi Nakajima et al., "Microbial Production of D–Valine from Racemic a–Aminoisovaleronitrile".
Chemical Abstracts, vol. 73, no. 13, CA 65041r, Sep. 28, 1970, Takeda, Hideo, "Fermentative preparation of D–amino acids".
Experientia, vol. 26, No. 1, 1970, pp. 37–38, Wickramasinghe, R. "Multiple Histidine Degrading Enzymes in Proteus vulgaris".

*Primary Examiner*—Herbert J. Lilling
*Attorney, Agent, or Firm*—Finnegan, Henderson, Farabow, Garrett & Dunner, L.L.P.

[57] ABSTRACT

Disclosed is a process for preparing a D-amino acid selected from the group consisting of D-methionine, D-valine, D-leucine, D-isoleucine and D-histidine, which comprises the steps of:

making a culture or treated culture of a microorganism having ability to asymmetrically degrade a L-amino acid selected from the group consisting of L-methionine, L-valine, L-leucine, L-isoleucine and L-histidine act on a corresponding racemic amino acid to the L-amino acid; and separating and collecting the remaining D-amino acid.

8 Claims, No Drawings

PROCESS FOR PREPARING D-AMINO ACIDS

BACKGROUND OF THE INVENTION

This invention relates to a novel process for preparing D-amino acids such as D-methionine, D-valine, D-leucine, D-isoleucine and D-histidine utilizing microorganisms.

D-Amino acids such as D-methionine, D-valine, D-leucine, D-isoleucine and D-histidine are useful compounds as starting materials or synthetic intermediates for preparation of various medicines such as antibiotics, or optically resolving agents. In the prior art, as a process for preparing these amino acids, there have been known a fractional crystallization method of a racemic material, an optical resolution method by chromatography and a physicochemical method such as an organochemical asymmetric synthesis and the like. As a biochemical method, there have been known a method of asymmetrically hydrolyzing N-acetyl-DL-amino acids by using a microorganism enzyme (Applied and Environmental Microbiology, vol. 54, pp. 984–989 (1988)), a method of asymmetrically hydrolyzing 5-methylthioethylhydantoin, 5-isopropylhydantoin, 5-isopentanoylhydantoin or 5-sec-butylhydantoin by using a microorganism enzyme (Journal of Fermentation Technology, vol. 56, pp. 492–498 (1978)), a method of asymmetrically hydrolyzing 5-(4-imidazolemethyl)-hydrantoin by using a microorganism enzyme (Agric. Biol. Chem., vol. 51, pp. 715–719 (1987)), a method of hydrolyzing D-N-carbamoyl-a-amino acids (PCT Patent Publication No. WO 92/10579), a method of asymmetrically hydrolyzing DL-aminonitrile by using a microorganism enzyme (Bull. Inst. Chem. Res., Kyoto Univ., vol. 65, pp. 141–143 (1987)) or a method of transferring an amino group of an $\alpha$-keto acid by using a microorganism enzyme (J. Biotechnol., vol. 8, pp. 243–248 (1988)).

In the above-mentioned physicochemical method, there are disadvantages that operation is complicated or troublesome, and yield and optical purity of the product are low. In the biochemical method, there are disadvantages that 5-methylthioethylhydantoin, 5-isopropylhydantoin, 5-isopentanoylhydantoin, 5-sec-butylhydantoin, 5-(4-imidazolemethyl)-hydrantoin and D-N-carbamoyl-α-amino acids which are used as a substrate are expensive, separation of the product is difficult and regeneration of coenzyme is required. Thus, it has been desired to develop a process for preparing a D-amino acid which solves at least one problems as mentioned above.

SUMMARY OF THE INVENTION

The present inventors have studied intensively and consequently found microorganisms having ability to selectively degrade only a L-isomer in a racemic amino acid, to accomplish the present invention.

That is, the present invention is a process for preparing a D-amino acid selected from the group consisting of D-methionine, D-valine, D-leucine, D-isoleucine and D-histidine, which comprises the steps of:

making a culture or treated culture of a microorganism having ability to asymmetrically degrade a L-amino acid selected from the group consisting of L-methionine, L-valine, L-leucine, L-isoleucine and L-histidine act on a corresponding racemic amino acid to said L-amino acid; and separating and collecting the remaining D-amino acid.

DESCRIPTION OF THE PREFERRED EMBODIMENTS

In the following, the present invention is explained in detail.

In the present specification, the term "amino acid" means a specific amino acid selected from the group consisting of methionine, valine, leucine, isoleucine and histidine.

The racemic amino acid to be used as a starting material in the present invention may be not only one containing equal amounts of D-isomer and L-isomer, but one containing both of these optical isomers in any ratio of mixture. As the racemic amino acid, racemic modifications of methionine, valine, leucine, isoleucine and histidine are used.

The microorganism to be used in the present invention may be any microorganism having ability to asymmetrically degrade at least one L-amino acid, i.e., ability to selectively degrade a L-isomer in a racemic amino acid.

As such a microorganism degrading L-methionine, there may be mentioned, for example, microorganisms belonging to Proteus, Providencia, Micrococcus or Morganella. Among them, preferred are microorganisms belonging to Proteus or Providencia (e.g., *Proteus vulgaris, Proteus mirabilis, Providencia rettgeri* and *Providencia alcalifaciens*), and particularly preferred are microorganisms belonging to Proteus.

Specific examples of these microorganisms include *Proteus vulgaris* IFO 3045, *Proteus vulgaris* RIMD KS (IAM 12003), *Proteus vulgaris* OUT 8144 (IFO 3851), *Proteus mirabilis* IFO 3849, *Providencia rettgeri* ATCC 29944, *Providencia rettgeri* IFO 13051, *Providencia rettgeri* ATCC 21118, *Providencia rettgeri* ATCC 25932, *Providencia rettgeri* ATCC 9919, *Providencia alcalifaciens* JCM 1673, *Micrococcus* sp. IAM 1012, *Morganella morganii* IFO 3848 or the like.

As a microorganism degrading L-valine, L-leucine or L-isoleucine, there may be mentioned, for example, microorganisms belonging to Achromobacter, Proteus, Providencia or Yarrowia. Among them, preferred are microorganisms belonging to Proteus or Providencia, and particularly preferred are microorganisms belonging to Proteus (e.g., *Proteus vulgaris*).

Specific examples of these microorganisms include *Achromobacter liguidum* OUT 8012 (FERM P-12684), *Proteus vulgaris* RIMD KS (IAM 12003), *Proteus vulgaris* AHU 1469, *Proteus vulgaris* AHU 1472, *Proteus vulgaris* AHU 1474, *Providencia alcalifaciens* JCM 1673, *Providencia rettgeri* ATCC 25932, *Yarrowia lipolytica* IFO 0717, *Yarrowia lipolytica* IFO 0746, *Yarrowia lipolytica* IFO 1195, *Yarrowia lipolytica* IFO 1209, *Yarrowia lipolytica* IFO 1548 or the like.

As a microorganism degrading L-histidine, there may be mentioned, for example, microorganisms belonging to Acinetobacter, Enterobacter, Klebsiella, Corynebacterium, Pseudomonas, Serratia, Bacillus, Hafnia, Paracoccus, Flavobacterium, Brevibacterium, Proteus, Providencia, Morganella, Candida, Hansenula or Saccharomyces. Among them, preferred are microorganisms belonging to Proteus or Providencia, and particularly preferred are microorganisms belonging to Proteus (e.g., *Proteus vulgaris*).

Specific examples of these microorganisms include *Acinetobacter calcoaceticus* IFO 12552, *Enterobacter aerogenes* IFO 12010, *Klebsiella pneumoniae* ATCC 10031, *Klebsiella pneumoniae* IFO 3317, *Corynebacterium alkanolyticum* ATCC 21511, *Pseudomonas aeruginosa* IAM 1220, *Pseudomonas aeruginosa* ATCC 7700, *Pseudomonas aeruginosa* IFO 3918, *Pseudomonas aureofaciens* IAM 1001, *Pseudomonas ovalis* IAM 1177, *Pseudomonas ovalis* IAM 1094, *Pseudomonas ovalis* IAM 1153, *Pseudomonas schuylkilliensis* IAM 1126, *Pseudomonas gelidicola* OUT 8116 (FERM P-14991), *Pseudomonas putida* ATCC 33015, *Pseudomonas fluorescens* IFO 3081, *Pseudomonas fluorescens* IAM 1219, *Pseudomonas fragi* OUT 8255, *Serratia plymuthica* IAM 1255, *Serratia marcescens* ATCC 14764, *Serratia marcescens* ATCC 19180, *Serratia marcescens* ATCC 27117, *Serratia marcescens* IAM 1104, *Serratia marcescens* IAM 12143, *Serratia marcescens* IAM 12359, *Serratia marcescens* IFO 3735, *Serratia marcescens* IFO 12648, *Serratia liquefaciens* ATCC 27592, *Bacillus coagulans* IFO 12714, *Hafnia alvei* IFO 3731, *Paracoccus denitrificans* IFO 12442, *Flavobacterium* sp. FERM P-6901, *Brevibacterium helvolum* IAM 1637, *Proteus vulgaris* RIMD KS (IAM 12003), *Proteus mirabilis* IFO 3849, *Providencia alcalifaciens* JCM 1673, *Providencia rettgeri* IFO 13501, *Providencia rettgeri* ATCC 21118, *Providencia rettgeri* ATCC 25932, *Providencia rettgeri* ATCC 9919, *Providencia rustigianii* JCM 3953, *Morganella morganii* IFO 3848, *Candida boidinii* IFO 10240, *Hansenula polymorpha* IFO 1024, *Saccharomyces cerevisiae* IFO 2342, *Saccharomyces cerevisiae* IFO 2345 or *Saccharomyces cerevisiae* IFO 2114, or the like.

Among the microorganisms mentioned above, as such a microorganism having ability to degrade any one of the group consisting of L-methionine, L-valine, L-leucine, L-isoleucine and L-histidine, there may be mentioned, for example, microorganism belonging to Proteus or Providencia. Between them, preferred are microorganism belonging to Proteus (e.g., *Proteus vulgaris*).

Specific examples of these microorganism include *Proteus vulgaris* RIMD KS (IAM 12003), *Providencia rettgeri* ATCC 25932, *Providencia alcalifaciens* JCM 1673 or the like.

The microorganism to be used in the present invention may be a strain which is newly separated from soil, food, an animal or the like so long as it has an ability necessary for the present invention. Further, there may be used a mutant obtained by artificial treatment such as irradiation of UV ray or treatment using a mutating agent or a strain derived from the above microorganism by a genetic engineering means such as recombination of DNA or cell fusion, or bioengineering means. For example, according to the genetic engineering means, a gene of an objective enzyme is isolated from a chromosome fragment of a microorganism producing an enzyme which has ability to asymmetrically degrade a L-amino acid, then a recombinant plasmid obtained by introducing the gene into an appropriate plasmid vector is formed, and an appropriate host microorganism is transformed by the recombinant plasmid to obtain a microorganism having ability to produce an enzyme or having an improved productivity of said enzyme. Further, a host microorganism having other excellent characteristics (e.g., easy in culture or the like) may be transformed by the recombinant plasmid, if necessary.

The culture or treated culture of the microorganism to be used in the present invention is any culture or treated culture so long as it has ability to asymmetrically degrade at least one of the above specific L-amino acids. As the culture, there may be mentioned, for example, a culture broth or a living cell, and as the treated culture, there may be mentioned, for example, a treated culture broth such as a culture supernatant, a treated cell such as a washed cell, a dried cell, a ground cell, an autolysate of a cell, an extract of a cell, or a partially purified enzyme or purified enzyme obtained therefrom according to the conventional manner.

The above culture (e.g., a culture broth, living cell or the like) can be obtained by, for example, culturing the microorganism in a medium (e.g., a conventional medium containing carbon source, nitrogen source and an inorganic salt), at pH about 5 to pH about 8 at ordinary temperature to under heating (preferably about 20° C. to 40° C.) and under aerobic conditions. Further, during culture, by adding about 0.001% to about 10%, preferably about 0.1% to about 2%, particularly about 0.1% to about 1% of an appropriate amino acid such as DL-methionine or DL-histidine to the medium, the desired enzyme activity can be enhanced.

The living cell and the culture supernatant can be prepared from the thus-obtained culture broth as described above, by means of such as centrifugation or filtration. The washed cell can be obtained by washing a living cell with a physiological saline, and the dried cell can be obtained by subjecting a living cell or a washed cell to lyophilization or acetone drying. The ground cell can be obtained by treating a living cell or a washed cell by various known physico-chemical methods, for example, ultrasonication, French press, osmotic pressure, freezing and thawing, alumina grinding or lysokinase, a surfactant or an organic solvent. The extract of a cell can be obtained by, for example, removing insoluble matters from a ground cell by filtration or centrifugation. The partially purified enzyme or purified enzyme can be obtained by, for example, fractionating an enzyme from a fraction of a pulverized cell or a culture supernatant according to a conventional manner such as fractionation using ammonium sulfate, ion exchange chromatography or gel filtration chromatography and purifying the enzyme by using ability to selectively degrade the above specific L-amino acid as an index.

The above microorganism cells, treated cells or enzymes may be used as such and may be used after immobilizing it by a polyacrylamide method, a sulfur-containing polysaccharide gel method (e.g., a carrageenan gel method), an alginic acid gel method, an agar gel method or the like.

Also, the microorganism which can asymmetrically degrade the L-amino acid is cultured in a medium containing the racemic amino acid and the D-amino acid remained in the medium may be separated and collected.

The asymmetric degradation according to the present invention can be carried out by bringing the racemic amino acid which is a starting compound into contact with the culture or treated culture of the microorganism having ability to asymmetrically degrade the L-amino acid in a solution, followed by incubation. Further, if desired, the reaction may be carried out concurrently with culturing the microorganism. In such a case, the reaction can be carried out by using a medium to which the racemic amino acid is previously added under the same conditions as those of culture.

The reaction can be carried out suitably in an aqueous solution. Further, the reaction proceeds suitably at ordinary temperature to under heating, preferably about 10° C. to about 50° C., particularly preferably about 25° C. to about 40° C. It is preferred to adjust the pH of the reaction mixture to pH about 5 to pH about 11, particularly pH about 6 to pH about 9.

The charged concentration (w/v) of the racemic amino acid which is a starting compound to be used as a reaction substrate is generally preferably about 0.05% to about 30 %, particularly about 1% to about 20%. The starting compound may be added at one time in the beginning or may be added several times with divided amounts during the reaction.

When the living cell is used in the present invention, it is preferred to add a surfactant to the reaction mixture since the reaction time can be shortened. As an example of the surfactant to be used for the above purpose, there may be mentioned cetyl pyridinium bromide, cetyl trimethylammonium bromide or p-isooctylphenyl ether (Triton X-100, trade name, produced by Rohm & Haas Co., U.S.A.), and it is preferred to use the surfactant in an amount of about 0.0001% to about 0.1% based on the amount of the reaction mixture.

After completion of the reaction, collection and isolation of the D-amino acid from the reaction mixture can be carried out easily according to the conventional manner. For example, after insoluble materials such as a cell are removed from the reaction mixture by centrifugation, the reaction mixture is treated with activated carbon to adsorb and remove a dye or the like and the mixture is concentrated under reduced pressure. Thereafter, the reaction mixture is subjected to crystallization under cooling to obtain crystals of the D-amino acid.

Detection whether or not the culture or the treated culture of the microorganism has ability to asymmetrically degrade the L-amino acid can be carried out easily according to the above reaction method, for example, as described below. That is, the culture or the treated culture of the microorganism to be detected is added to a medium or aqueous solution containing the racemic amino acid, and the mixture is shaken at 30° C. for 120 hours. The solution after completion of the reaction is analyzed and quantitated by high performance liquid chromatography using an optically active column (e.g., CROWNPAK CR(+), trade name, manufactured by Daicel Kagaku Kogyo Co. or SUMICHIRAL OA-5000, trade name, manufactured by Sumika Analysis Center) to measure the respective contents of the D-amino acid and the L-amino acid. By the measurement, for example, when it is found that a L-isomer is reduced and a D-isomer remains in the reaction mixture, it is judged that the culture or the treated culture of the microorganism has ability to asymmetrically degrade the L-amino acid.

EXAMPLES

The present invention is described in detail by referring to Examples, but should not be construed to be limited thereto.

In the present specification, "%" always means "weight/volume (g/dl)". Further, in Examples, quantitation of an optical isomer of methionine was carried out by high performance liquid chromatography using CROWNPAK CR(+) (trade name, manufactured by Daicel Kagaku Kogyo Co.) and other amino acids by high performance liquid chromatography using SUMICHIRAL OA-5000 (trade name, manufactured by Sumika Analysis Center).

Example 1

Into a shaking flask having a volume of 500 ml was charged 100 ml of a medium (pH 7.0) comprising 2% of DL-methionine, 0.2% of ammonium sulfate, 0.1% of potassium dihydrogen phosphate, 0.05% of magnesium sulfate and 0.02% of a yeast extract, and the medium was sterilized at 120° C. for 10 minutes. A loopful of Proteus vulgaris IFO 3045 was inoculated into the medium, and cultured at 30° C. for 168 hours with shaking. The cells were removed by centrifuging 1000 ml of the above culture broth to obtain a supernatant. Ultrafiltration was carried out in order to remove protein and others in the above supernatant, whereby a filtrate was obtained. After activated carbon was added to the filtrate to effect decolorization, the filtrate was concentrated under reduced pressure, and the concentrate was crystallized by cooling to obtain 4.8 g of crystals of D-methionine.

Optical rotation: $[\alpha]_D^{20}$: −23.1° (C=2, 6N HCl)

Optical purity: 100%

Example 2

Into 100 ml of the medium shown in Example 1 were inoculated microorganisms in Table 1 shown below, respectively. After the microorganisms were cultured while shaking at 30° C. for 120 hours, D-methionine remaining in the culture broth was quantitated. The contents of D-methionine were as shown in Table 1. Further, almost no L-methionine which was an antipode was detected from the culture broth.

TABLE 1

| Name of strain | Remaining D-methionine (mg/ml) |
| --- | --- |
| Proteus vulgaris IFO 3045 | 10.0 |
| Proteus vulgaris RIMD KS (IAM 12003) | 10.0 |
| Micrococcus sp. IAM 1012 | 9.3 |
| Proteus mirabilis IFO 3849 | 9.0 |
| Morganella morganii IFO 3848 | 8.1 |
| Providencia rettgeri ATCC 29944 | 5.6 |
| Providencia rettgeri IFO 13501 | 7.6 |
| Providencia rettgeri ATCC 21118 | 6.9 |
| Providencia rettgeri ATCC 25932 | 7.6 |
| Providencia rettgeri ATCC 9919 | 7.6 |

Example 3

Into a shaking flask having a volume of 500 ml was charged 100 ml of a medium (pH 7.0) comprising 0.5% of DL-methionine, 1.0% of polypeptone, 1.0% of a yeast extract and 0.5% of sodium chloride, and the medium was sterilized at 120° C. for 10 minutes. A loopful of Proteus vulgaris RIMD KS (IAM 12003) was inoculated into the medium and cultured at 30° C. for 20 hours with shaking. The cells collected from 1000 ml of the above culture broth by centrifugation were suspended in a physiological saline and the suspension was further centrifuged to collect cells. To the cells was added 500 ml of a 50 mM phosphate buffer (pH 7.0) containing 10% of DL-methionine, and the mixture was reacted at 30° C. for 72 hours to degrade L-methionine completely.

After the reaction, the cells were removed by centrifugation, and subsequent procedures were carried out in the same manner as in Example 1 to obtain 13.3 g of D-methionine.

Optical rotation: $[\alpha]_D^{20}$: −23.2° (C=2, 6N HCl)

Optical purity: 100%

Example 4

A loopful of a microorganism shown in the following Table 2 was inoculated into the medium shown in Example 3 and cultured at 30° C. for 20 hours with shaking. The cells collected from 100 ml of the above culture broth by centrifugation were suspended in a physiological saline and the suspension was further centrifuged to collect cells. To the cells was added 50 ml of a 50 mM phosphate buffer (pH 7.0) containing 4% of DL-methionine, and the mixture was reacted at 30° C. for 120 hours. The contents of D-methionine of the reaction mixtures were as shown in Table 2.

Further, almost no L-methionine which was an antipode was detected from the reaction mixtures.

TABLE 2

| Name of strain | Remaining D-methionine (mg/ml) |
| --- | --- |
| *Proteus vulgaris* IFO 3045 | 20.0 |
| *Proteus vulgaris* RIMD KS (IAM 12003) | 20.0 |
| *Proteus vulgaris* OUT 144 (IFO 3851) | 19.3 |
| *Providencia alcalifaciens* JCM 1673 | 9.3 |

Example 5

Into a test tube was charged 3 ml of a medium (pH 7.0) comprising 2% of DL-valine, 0.5% of ammonium sulfate, 0.1% of potassium dihydrogen phosphate, 0.05% of magnesium sulfate and 0.02% of a yeast extract, and the medium was sterilized at 120° C. for 10 minutes. Into the medium were inoculated microorganisms in Table 3 shown below, respectively. After the microorganisms were cultured while shaking at 30° C. for 144 hours, D-valine remaining in the culture broth was quantitated. The contents of D-valine were as shown in Table 3. Further, almost no L-valine which was an antipode was detected from the culture broth.

TABLE 3

| Name of strain | Remaining D-valine (mg/ml) |
| --- | --- |
| *Achromobacter liquidum* OUT 8012 (FERM P-12684) | 3.8 |
| *Proteus vulgaris* RIMD KS (IAM 12003) | 7.3 |
| *Proteus vulgaris* AHU 1469 | 8.3 |
| *Proteus vulgaris* AHU 1472 | 8.0 |
| *Proteus vulgaris* AHU 1474 | 7.1 |

Example 6

Into a shaking flask having a volume of 500 ml was charged 100 ml of a medium (pH 7.0) comprising 0.5% of DL-methionine, 1.0% of polypeptone, 1.0% of a yeast extract and 0.5% of sodium chloride, and the medium was sterilized at 120° C. for 10 minutes. A loopful of Proteus vulgaris RIMD KS (IAM 12003) was inoculated into the medium, and cultured at 30° C. for 20 hours with shaking. The cells collected by centrifuging 1600 ml of the above culture broth were suspended in a physiological saline and the suspension was further centrifuged to collect cells. To the cells was added 800 ml of a 50 mM phosphate buffer (pH 7.0) containing 5% of DL-valine, and the mixture was reacted at 30° C. for 72 hours to effect asymmetric degradation to completely degrade L-valine. After the reaction, the mixture was sterilized by centrifugation to obtain a supernatant. Ultrafiltration was carried out in order to remove protein and others in the above supernatant, whereby a filtrate was obtained. The filtrate was concentrated under reduced pressure, and the concentrate was crystallized by cooling to obtain 4.0 g of crystals of D-valine.

Optical rotation: $[\alpha]_D^{20}$: −27.5° (C=8, 6N HCl)

Optical purity: 100%

Example 7

Into 3 ml of the sterilized medium (pH 7.0) comprising 0.5% of DL-valine, 1.0% of polypeptone, 1.0% of a yeast extract and 0.5% of sodium chloride were inoculated microorganisms in Table 4 shown below, respectively, and cultured at 30° C. for 20 hours with shaking. Cells collected by centrifuging 3 ml of the above culture were suspended in physiological saline and the suspension was further centrifuged to collect cells. To the cells was added 2 ml of a 50 mM phosphate buffer (pH 7.0) containing 5% of DL-valine, and the mixture was reacted at 30° C. for 144 hours to effect asymmetric degradation. The contents of D-valine were as shown in Table 4. Further, almost no L-valine which was an antipode was detected from the reaction mixture.

TABLE 4

| Name of strain | Remaining D-valine (mg/ml) |
| --- | --- |
| *Achromobacter liguidum* OUT 8012 (FERM P-12684) | 19.5 |
| *Proteus vulgaris* RIMD RS (IAM 12003) | 20.8 |
| *Proteus vulgaris* AHU 1469 | 20.6 |
| *Proteus vulgaris* AHU 1472 | 15.2 |
| *Proteus vulgaris* AHU 1474 | 22.5 |
| *Providencia alcalifaciens* JCM 1673 | 22.3 |
| *Providencia rettgeri* ATCC 25932 | 19.2 |
| *Yarrowia lipolytica* IFO 0717 | 23.7 |
| *Yarrowia lipolytica* IFO 1195 | 22.2 |
| *Yarrowia lipolytica* IFO 1209 | 19.4 |

Example 8

Into a test tube was charged 3 ml of a medium (pH 7.0) comprising 1% of DL-leucine, 1% of a yeast extract, 1% of polypeptone and 0.5% of sodium chloride, and the medium was sterilized at 120° C. for 10 minutes. Into the medium were inoculated microorganisms in Table 5 shown below, respectively. After the microorganisms were cultured while shaking at 30° C. for 24 hours, D-leucine remaining in the culture broth was quantitated. The contents of D-leucine were as shown in Table 5. Further, almost no L-leucine which was an antipode was detected from the culture broth.

TABLE 5

| Name of strain | Remaining D-leucine (mg/ml) |
| --- | --- |
| *Achromobacter liquidum* OUT 8012 (FERM P-12684) | 4.5 |
| *Proteus vulgaris* RIMD KS (IAM 12003) | 4.2 |
| *Proteus vulgaris* AHU 1469 | 5.0 |
| *Proteus vulgaris* AHU 1472 | 5.0 |
| *Proteus vulgaris* AHU 1474 | 3.2 |
| *Yarrowia lipolytica* IFO 1548 | 5.0 |
| *Yarrowia lipolytica* IFO 1209 | 5.0 |

Example 9

Into a shaking flask having a volume of 500 ml was charged 100 ml of a medium (pH 7.0) comprising 0.5% of DL-methionine, 1.0% of polypeptone, 1.0% of a yeast extract and 0.5% of sodium chloride, and the medium was sterilized at 120° C. for 10 minutes. A loopful of Proteus vulgaris RIMD KS (IAM 12003) was inoculated into the medium and cultured at 30° C. for 20 hours with shaking. The cells collected from 1600 ml of the above culture broth by centrifugation were suspended in a physiological saline and then the suspension was further centrifuged to collect cells. To the cells was added 800 ml of a 50 mM phosphate buffer (pH 7.0) containing 5% of DL-leucine, and the mixture subjected to asymmetric degradation at 30° C. for 72 hours to degrade L-leucine completely. After the reaction, the cells were removed by centrifugation, and subsequent procedures were carried out in the same manner as in Example 6 to obtain 5.3 g of D-leucine.

Optical rotation: $[\alpha]_D^{20}$: −15.3° (C=4, 6N HCl)
Optical purity: 100%

Example 10

Into a test tube was charged 3 ml of a medium (pH 7.0) comprising 1% of DL-leucine, 1% of a yeast extract, 1% of polypeptone and 0.5% of sodium chloride, and the medium was sterilized at 120° C. for 10 minutes. Into the medium were inoculated microorganisms in Table 6 shown below, respectively. After the microorganisms were cultured while shaking at 30° C. for 24 hours, cells collected by centrifugation were suspended in a physiological saline and the suspension was further centrifuged to collect cells. To the cells was added 2 ml of a 50 mM phosphate buffer (pH 7.0) containing 1% of DL-leucine, and the mixture was reacted at 30° C. for 24 hours to effect asymmetric degradation. The contents of D-leucine were as shown in Table 6. Further, almost no L-leucine which was an antipode was detected from the reaction mixture.

TABLE 6

| Name of strain | Remaining D-leucine (mg/ml) |
|---|---|
| Achromobacter liguidum OUT 8012 (FERM P-12684) | 4.1 |
| Proteus vulgaris RIMD KS (IAM 12003) | 4.5 |
| Proteus vulgaris AHU 1469 | 4.5 |
| Proteus vulgaris AHU 1472 | 4.0 |
| Proteus vulgaris AHU 1474 | 4.7 |
| Providencia alcalifaciens JCM 1673 | 4.4 |
| Yarrowia lipolytica IFO 0717 | 1.8 |

Example 11

Into a test tube was charged 3 ml of a medium (pH 7.0) comprising 1% of DL-isoleucine, 1% of a yeast extract, 1% of polypeptone and 0.5% of sodium chloride, and the medium was sterilized at 120° C. for 10 minutes. Into the medium were inoculated microorganisms in Table 7 shown below, respectively. After the microorganisms were cultured while shaking at 30° C. for 24 hours, D-isoleucine remaining in the culture broth was quantitated. The contents of D-isoleucine were as shown in Table 7. Further, almost no L-isoleucine which was an antipode was detected from the culture broth.

TABLE 7

| Name of strain | Remaining D-isoleucine (mg/ml) |
|---|---|
| Achromobacter liquidum OUT 8012 (FERM P-12684) | 3.9 |
| Proteus vulgaris RIMD KS (IAM 12003) | 3.4 |
| Proteus vulgaris AHU 1469 | 3.6 |
| Proteus vulgaris AHU 1472 | 3.5 |
| Proteus vulgaris AHU 1474 | 3.9 |
| Providencia alcalifaciens JCM 1673 | 3.5 |
| Yarrowia lipolytica IFO 1209 | 3.4 |

Example 12

Into a shaking flask having a volume of 500 ml was charged 100 ml of a medium (pH 7.0) comprising 0.5% of DL-methionine, 1.0% of polypeptone, 1.0% of a yeast extract and 0.5% of sodium chloride, and the medium was sterilized at 120° C. for 10 minutes. A loopful of Proteus vulgaris RIMD KS (IAM 12003) was inoculated into the medium, and cultured at 30° C. for 20 hours with shaking. The cells collected from 1600 ml of the above culture broth by centrifugation were suspended in a physiological saline and then the suspension was further centrifuged to collect cells. To the cells was added 800 ml of a 50 mM phosphate buffer (pH 7.0) containing 5% of DL-isoleucine, and the mixture subjected to asymmetric degradation at 30° C. for 72 hours to degrade L-isoleucine completely. After the reaction, the cells were removed by centrifugation, and subsequent procedures were carried out in the same manner as in Example 6 to obtain 8.5 g of D-isoleucine.

Optical rotation: $[\alpha]_D^{20}$: −38.0° (C=4, 6N HCl)
Optical purity: 100%

Example 13

Into a test tube was charged 3 ml of a medium (pH 7.0) comprising 1% of DL-isoleucine, 1% of a yeast extract, 1% of polypeptone and 0.5% of sodium chloride, and the medium was sterilized at 120° C. for 10 minutes. Into the medium were inoculated microorganisms in Table 8 shown below, respectively. After the microorganisms were cultured while shaking at 30° C. for 24 hours, cells collected by centrifugation were suspended in a physiological saline and the suspension was further centrifuged to collect cells. To the cells was added 2 ml of a 50 mM phosphate buffer (pH 7.0) containing 2% of DL-isoleucine, and the mixture was reacted at 30° C. for 24 hours to effect asymmetric degradation. The contents of D-isoleucine were as shown in Table 8. Further, almost no L-isoleucine which was an antipode was detected from the reaction mixture.

TABLE 8

| Name of strain | Remaining D-isoleucine (mg/ml) |
|---|---|
| Achromobacter liguidum OUT 8012 (FERM P-12684) | 8.1 |
| Proteus vulgaris AHU 1469 | 9.0 |
| Proteus vulgaris AHU 1472 | 8.9 |
| Proteus vulgaris AHU 1474 | 9.2 |
| Providencia alcalifaciens JCM 1673 | 9.0 |
| Yarrowia lipolytica IFO 0717 | 9.6 |
| Yarrowia lipolytica IFO 1548 | 8.6 |
| Yarrowia lipolytica IFO 0746 | 7.9 |
| Yarrowia lipolytica IFO 1195 | 8.6 |
| Yarrowia lipolytica IFO 1209 | 4.8 |

Example 14

Into a test tube was charged 3 ml of a medium (pH 7.0) comprising 2% of DL-histidine, 0.5% of ammonium sulfate, 0.1% of potassium dihydrogen phosphate, 0.05% of magnesium sulfate and 0.02% of a yeast extract, and the medium was sterilized at 120° C. for 10 minutes. Into the medium were inoculated microorganisms in Table 9 shown below, respectively, and the microorganisms were cultured while shaking at 30° C. for 168 hours, D-histidine remaining in the culture broth was quantitated. The contents of D-histidine were as shown in Table 9, respectively. Further, almost no L-histidine which was an antipode was detected from the culture broth.

TABLE 9

| Name of strain | Remaining D-histidine (mg) |
|---|---|
| Acinetobacter calcoaceticus IFO 12552 | 17.7 |
| Enterobacter aerogenes IFO 12010 | 26.6 |
| Klebsiella pneumoniae ATCC 10031 | 24.2 |
| Klebsiella pneumoniae IFO 3317 | 30.0 |
| Corynebacterium alkanolyticum ATCC 21511 | 30.0 |
| Pseudomonas aeruginosa IAM 1220 | 30.0 |
| Pseudomonas aeruginosa ATCC 7700 | 28.3 |
| Pseudomonas aeruginosa IFO 3918 | 23.5 |
| Pseudomonas aureofaciens IAM 1001 | 30.0 |
| Pseudomonas ovalis IAM 1177 | 26.4 |
| Pseudomonas ovalis IAM 1094 | 28.1 |
| Pseudomonas ovalis IAM 1153 | 26.6 |
| Pseudomonas schuylkilliensis IAM 1126 | 28.9 |
| Pseudomonas gelidicola OUT 8116 (FERM P-14991) | 26.2 |
| Pseudomonas putida ATCC 33015 | 30.0 |
| Pseudomonas fluorescens IFO 3081 | 27.0 |
| Pseudomonas fluorescens IAM 1219 | 27.0 |
| Pseudomonas fragi OUT 8255 | 28.7 |
| Serratia plymuthica IAM 1255 | 23.2 |
| Serratia marcescens ATCC 14764 | 28.8 |
| Serratia marcescens ATCC 19180 | 26.6 |
| Serratia marcescens ATCC 27117 | 27.5 |
| Serratia marcescens IAM 1104 | 28.5 |
| Serratia marcescens IAM 12143 | 25.1 |
| Serratia marcescens IAM 12359 | 30.0 |
| Serratia marcescens IFO 3735 | 27.5 |
| Serratia marcescens IFO 12648 | 22.2 |
| Serratia liquefaciens ATCC 27592 | 20.3 |
| Bacillus coagulans IFO 12714 | 24.7 |
| Hafnia alvei IFO 3731 | 18.5 |
| Paracoccus denitrificans IFO 12442 | 23.9 |
| Flavobacterium sp. FERM P-6901 | 28.0 |
| Brevibacterium helvolum IAM 1637 | 22.1 |
| Proteus vulgaris RIMD KS (IAM 12003) | 30.0 |
| Proteus mirabilis IFO 3849 | 29.9 |
| Providencia alcalifaciens JCM 1673 | 28.8 |
| Providencia rettgeri IFO 13501 | 30.0 |
| Providencia rettgeri ATCC 21118 | 30.0 |
| Providencia rettgeri ATCC 25932 | 30.0 |
| Providencia rettgeri ATCC 9919 | 25.6 |
| Providencia rustigianii JCM 3953 | 28.1 |
| Morganella morganii IFO 3848 | 27.5 |
| Candida boidinii IFO 10240 | 30.0 |
| Hansenula polymorpha IFO 1024 | 30.0 |
| Saccharomyces cerevisiae IFO 2342 | 30.0 |
| Saccharomyces cerevisiae IFO 2345 | 30.0 |
| Saccharomyces cerevisiae IFO 2114 | 30.0 |

Example 15

Into a shaking flask having a volume of 500 ml was charged 100 ml of a medium (pH 7.0) comprising 0.5% of DL-histidine, 1.0% of polypeptone, 1.0% of a yeast extract and 0.5% of sodium chloride, and the medium was sterilized at 120° C. for 10 minutes. A loopful of Proteus vulgaris RIMD KS (IAM 12003) was inoculated into the medium, and cultured at 30° C. for 20 hours with shaking. The cells collected from 2000 ml of the above culture broth by centrifugation were suspended in a physiological saline and then the suspension was further centrifuged to collect cells. To the cells was added 800 ml of a 50 mM phosphate buffer (pH 7.0) containing 10% of DL-histidine, and the mixture subjected to asymmetric degradation at 30° C. for 48 hours to degrade L-histidine completely. After the reaction, the cells were removed by centrifuging the above culture broth to obtain a supernatant. Ultrafiltration was carried out in order to remove protein and others in the above supernatant, whereby a filtrate was obtained. The filtrate was decolorized by adding activated carbon to obtain a decolorized solution. The decolorized solution was passed through an ion exchange resin (Diaion SK116, trade name, produced by Mitsubishi Chemical Corporation) to adsorb the product. The adsorbed product was eluted with aqueous ammonia, and the resulting eluate was concentrated under reduced pressure, and the concentrate was crystallized by cooling to obtain 13.6 g of crystals of D-histidine.

Optical rotation: $[\alpha]_D^{20}$: −11.9° (C=11, 6N HCl)

Optical purity: 100%

Example 16

Into 3 ml of the sterilized medium (pH 7.0) comprising 1.0% of DL-histidine, 1.0% of polypeptone, 1.0% of a yeast extract and 0.5% of sodium chloride were inoculated microorganisms in Table 10 shown below, respectively, and the microorganisms were cultured while shaking at 30° C. for 20 hours. Cells collected from 3 ml of the above culture broth by centrifugation were suspended in a physiological saline and the suspension was further centrifuged to collect cells. To the cells was added 2 ml of a 50 mM phosphate buffer (pH 7.0) containing 10% of DL-histidine, and the mixture was reacted at 30° C. for 168 hours to effect asymmetric degradation. The contents of D-histidine in the reaction mixture were as shown in Table 10. Further, almost no L-histidine which was an antipode was detected from the reaction mixture.

TABLE 10

| Name of strain | Remaining D-histidine (mg) |
|---|---|
| Pseudomonas gelidicola OUT 8116 (FERM P-14991) | 82.1 |
| Proteus vulgaris RIMD KS (IAM 12003) | 90.6 |
| Proteus mirabilis IFO 3849 | 95.5 |
| Morganella morganii IFO 3848 | 86.2 |
| Providencia alcalifaciens JCM 1673 | 96.6 |
| Providencia rettgeri ATCC 21118 | 76.9 |
| Providencia rettgeri ATCC 9919 | 76.5 |

As described above, according to the process of the present invention, the D-amino acids can be prepared industrially from an inexpensive racemic amino acids with extremely good efficiency and high optical purity. Thus, the process of the present invention is an industrially advantageous preparation process.

We claim:

1. A process for preparing a D-amino acid selected from the group consisting of D-valine, D-leucine and D-isoleucine, which comprises the steps of:

making a culture or treated culture of a microorganism, having ability to asymmetrically degrade a L-amino acid selected from the group consisting of L-valine, L-leucine and L-isoleucine, which acts on a racemic amino acid corresponding to said L-amino acid; and separating and collecting the remaining D-amino acid;

wherein the microorganism belongs to Proteus, Providencia or Yarrowia.

2. The process according to claim 1, wherein the microorganism belongs to Proteus vulgaris, Providencia alcalifaciens, Providencia rettgeri or Yarrowia lipolytica.

3. The process according to claim 1, wherein the microorganism is at least one selected from the group consisting of Proteus vulgaris RIMD KS (IAM 12003), Providencia alcalifaciens JCM 1673, Providencia rettgeri ATCC 25932, Yarrowia lipolytica IFO 0717, Yarrowia lipolytica IFO 0746,

*Yarrowia lipolytica* IFO 1195, *Yarrowia lipolytica* IFO 1209 and *Yarrowia lipolytica* IFO 1548.

4. The process according to claim 1, wherein the step of making a culture or treated culture of a microorganism having ability to asymmetrically degrade the L-amino acid act on a racemic amino acid is carried out in a medium concurrently with culturing the microorganism having ability to asymmetrically degrade the L-amino acid.

5. The process according to claim 1, wherein making a culture or treated culture of a microorganism having ability to asymmetrically degrade the L-amino acid act on a racemic amino acid is carried out in an aqueous solution under about 10° C. to about 50° C. at pH about 5 to pH about 9.

6. The process according to claim 1, wherein making a culture or treated culture of a microorganism having ability to asymmetrically degrade the L-amino acid act on a racemic amino acid is carried out in an aqueous solution under about 25° C. to about 40° C. at pH about 6 to pH about 9.

7. The process according to claim 1, wherein the racemic amino acid is added to a medium in an amount of about 0.05% to about 30% in terms of w/v.

8. The process according to claim 1, wherein the racemic amino acid is added to a medium in an amount of about 1% to about 20% in terms of w/v.

* * * * *